(12) United States Patent
Kang et al.

(10) Patent No.: US 11,842,493 B2
(45) Date of Patent: Dec. 12, 2023

(54) METHOD AND APPARATUS FOR PREDICTING BRAIN DISEASE CHANGE THROUGH MACHINE LEARNING AND PROGRAM FOR THE SAME

(71) Applicants: THE ASAN FOUNDATION, Seoul (KR); UNIVERSITY OF ULSAN FOUNDATION FOR INDUSTRY COOPERATION, Ulsan (KR)

(72) Inventors: Dong Wha Kang, Seoul (KR); Young Hwan Kim, Seoul (KR)

(73) Assignees: THE ASAN FOUNDATION, Seoul (KR); UNIVERSITY OF ULSAN FOUNDATION FOR INDUSTRY COOPERATION, Ulsan (KR)

( * ) Notice: Subject to any disclaimer, the term of this patent is extended or adjusted under 35 U.S.C. 154(b) by 810 days.

(21) Appl. No.: 16/938,773

(22) Filed: Jul. 24, 2020

(65) Prior Publication Data
US 2020/0357120 A1 Nov. 12, 2020

Related U.S. Application Data

(63) Continuation of application No. PCT/KR2019/001095, filed on Jan. 25, 2019.

(30) Foreign Application Priority Data

Jan. 25, 2018 (KR) .................. 10-2018-0009618

(51) Int. Cl.
*G06T 7/00* (2017.01)
*G16H 20/17* (2018.01)
(Continued)

(52) U.S. Cl.
CPC .......... *G06T 7/0016* (2013.01); *A61B 5/0042* (2013.01); *A61B 5/02042* (2013.01);
(Continued)

(58) Field of Classification Search
None
See application file for complete search history.

(56) References Cited

U.S. PATENT DOCUMENTS

2018/0268942 A1* 9/2018 Kamali-Zare ........ A61B 5/4082

FOREIGN PATENT DOCUMENTS

JP 2014-042684 A 3/2014
KR 10-2016-0125840 A 5/2010
(Continued)

OTHER PUBLICATIONS

Park, Sang Cheol et al. Machine Learning for Medical Image Analysis, Journal of KIISE. Mar. 2012, vol. 39, No. 3, pp. 163-174.
(Continued)

*Primary Examiner* — Leon Flores
(74) *Attorney, Agent, or Firm* — Studebaker & Brackett PC

(57) ABSTRACT

A method for predicting brain disease state change is disclosed. The method includes acquiring test images obtained by capturing a portion of a human brain at a time interval, performing a pre-processing procedure of converting the test images into test voxels configured to be processed for image analysis, wherein a respective test voxel of the test voxels is composed of three-dimensional voxel units, mapping first and second test voxels selected from the test voxels acquired from a patient, with each other on a three-dimensional voxel unit, wherein the first test voxel is acquired at a first time-point and the second test voxel is acquired at a second time-point, generating a voxel-based data-set based on the mapped first and second test voxels, extracting a change in the test voxels using a deep neural network, and generating a state change probability model based on the change in the test voxels.

11 Claims, 11 Drawing Sheets
(6 of 11 Drawing Sheet(s) Filed in Color)

(51) Int. Cl.
*G16H 50/50* (2018.01)
*G16H 50/30* (2018.01)
*G16H 50/20* (2018.01)
*G16H 30/40* (2018.01)
*A61B 5/00* (2006.01)
*A61B 5/02* (2006.01)
*A61B 5/026* (2006.01)
*G06N 7/01* (2023.01)

(52) U.S. Cl.
CPC .......... *A61B 5/0263* (2013.01); *A61B 5/4842* (2013.01); *A61B 5/7275* (2013.01); *G06N 7/01* (2023.01); *G16H 20/17* (2018.01); *G16H 30/40* (2018.01); *G16H 50/20* (2018.01); *G16H 50/30* (2018.01); *G16H 50/50* (2018.01); *A61B 2576/026* (2013.01); *G06T 2207/10088* (2013.01); *G06T 2207/20076* (2013.01); *G06T 2207/30016* (2013.01)

(56) References Cited

FOREIGN PATENT DOCUMENTS

| | | |
|---|---|---|
| KR | 10-2016-0095426 A | 8/2016 |
| KR | 10-1740464 B1 | 6/2017 |
| KR | 10-1754291 B1 | 7/2017 |

OTHER PUBLICATIONS

International Search Report issued in PCT/KR2019/001095; dated May 9, 2019.

\* cited by examiner

METHOD AND APPARATUS FOR PREDICTING BRAIN DISEASE CHANGE THROUGH MACHINE LEARNING AND PROGRAM FOR THE SAME

CROSS-REFERENCE TO RELATED APPLICATIONS

The present application is a continuation of International Patent Application No. PCT/KR2019/001095, filed on Jan. 25, 2019, which is based upon and claims the benefit of priority to Korean Patent Application No. 10-2018-0009618, filed on Jan. 25, 2018. The disclosures of the above-listed applications are hereby incorporated by reference herein in their entirety.

BACKGROUND

Embodiments of the inventive concept described herein relate to a method, an apparatus, and a program for predicting brain disease state change through machine learning.

Thrombus is a product of metabolic processes in which production and decomposition are naturally balanced during an in vivo reaction and is associated with blood clotting. The blood clotting may occur in an event of blood composition change, for example, an increase in the number of platelets in the blood and an increase in fibrinogen due to damage to a blood vessel wall and change in a blood flow rate after surgery.

Cause of the production of thrombus has not yet been accurately identified. However, congenital genetic diseases such as disseminated intravascular coagulation (DIC), changes in a physiological function due to aging of a body, stress, etc., are being determined as the cause. In particular, stress caused by excessive work of modern people changes an amount of a factor involved in a blood clotting mechanism, and thus, thrombus is regarded as one of the causes of abnormal thrombus.

Thrombus is a substance that is generated as part of a hemostatic action. The hemostasis occurs when blood vessels are damaged, such that the blood vessels contract and an inner diameter thereof is narrowed and blood coagulating factors are involved to coagulate blood. The hemostasis process may be largely divided into 4 stages: 1) contraction of blood vessels, 2) thrombus formation caused by aggregation of platelets, 3) blood coagulating, and 4) proliferation of a fibrous tissue in the coagulated blood in this order. That is, platelets and tissues gather on collagen exposed at a wound site of blood vessels, and thus blood clotting begins and then the fibrous tissue proliferates in this site to clog the blood vessels. The thrombus thus formed is responsible for cerebrovascular disease such as stroke.

The stroke is a disease that accounts for 1st and 2nd causes of disability in Korea as a single disease. The stroke is divided into cerebral infarction and intracerebral hemorrhage. In the cerebral infarction, thrombus accumulated in blood vessels blocks blood supply to cause brain cell damage. The intracerebral hemorrhage refers to a symptom of bleeding due to damage to the blood vessel walls. Thrombolysis is an only treatment that may restore neurological deficits in a hyperacute stage of the cerebral infarction, but may lead to serious side effects such as intracerebral hemorrhage and bleeding spread.

Once onset, the stroke leaves irreversible neurological damage whose healing is impossible. Thus, cause analysis and prevention thereof are of the utmost importance. For this reason, many risk factors have been actively studied.

In general, it is known that it is determined whether a patient suffering from the cerebral infarction disease may ride a wheelchair or walk due to a difference of about 10% degree of an infarction region. Measuring a size of the infarction region accurately is recognized as an important factor in determining a degree of the cerebral infarction disease.

The stroke treatment guidelines provided from the Stroke Clinical Research Center in Korea specify recommendations according to a level of evidence and a grade of recommendation for intravenous thrombolysis and intra-arterial thrombolysis treatment. In an example, according to the stroke treatment guidelines prior to injection of a thrombolytic agent, a ⅓ rule is proposed to check whether a size of an initial brain lesion is more than ⅓ of a brain hemisphere. This rule is based on a research that the greater the brain lesion size, the higher a risk compared to a treatment gain. In conventional clinical sites, the brain lesion ⅓ rule is performed with a visual rating scheme or the size is drawn and quantified manually. Thus, reliability (reproducibility) and accuracy between evaluators are low.

A rapid thrombolytic treatment may lead to good prognosis. However, a risk of cerebral hemorrhage due to various factors has been inherent, and thus the thrombolytic treatment has been limitedly applied to patients within 4.5 hours from the onset. A bleeding spread prediction method considering complex risk factors before the thrombolytic treatment is very important and essential. However, there is a problem that the bleeding spread prediction method relies on subjective interpretation of a doctor in conventional clinical sites. Accordingly, an objective rationale and a quantitative analysis tool may be needed to help the doctor determine the treatment strategy.

Recently, as machine learning becomes an issue, a need for big data is emerging. Generally, the big data is recognized as a lot of patient data. Thus, conventional studies have used patient-level observations as an input into the machine learning. However, patient-level prognosis evaluation results in ignoring various internal prognosis of the patient. For example, even when only a portion of a patient's brain lesion has bleeding, information about a brain lesion that will not have the bleeding is determined as bleeding prognosis. This acts as a factor that degrades performance of an automatic classifier in the machine learning. Moreover, when machine learning on a patient-by-patient basis is used, it is difficult for a user who checks the learning results to intuitively grasp on a reason based on which the result is derived. Therefore, machine learning at a precise level via identification of a detailed bleeding spread pattern occurring in the patient and prognosis evaluation thereof may be necessary.

SUMMARY

Embodiments of the inventive concept provide a method, an apparatus, and a program for predicting brain disease state change through machine learning.

Embodiments of the inventive concept visualize recommendations for treatment of an acute stage of a stroke, using medical images and clinical information of patients with a hyperacute stage of the infarction. Treatment methods of the acute stage of the stroke may include intravenous or intra-arterial thrombolysis. Although not specified herein, each treatment method of the acute stage of the stroke includes visualizing recommendations for each treatment, a recommendation grade, and indications for each treatment method.

Embodiments of the inventive concept provide a method for establishing a state change probability model after the treatment of the acute stage of the stroke via machine learning using medical images and clinical information of patients with a hyperacute stage of the infarction, and a method for visualizing the state change probability model.

Embodiments of the inventive concept model a probability of bleeding spread on a voxel basis, based on machine learning using clinical information and initial/tracked medical images of patients with a hyperacute stage of the infarction, in establishing the state change probability model, and provide an user with an image of the probability of the bleeding spread after thrombolytic treatment of the hyperacute stage of the infarction using only the initial medical image.

The purpose of the present disclosure is not limited thereto. Other purposes as not mentioned will be clearly understood by those skilled in the art from following descriptions.

According to an exemplary embodiment, a method for predicting brain disease state change, as performed by a brain disease prediction apparatus includes acquiring, by the brain disease prediction apparatus, a plurality of test images, which comprise images obtained by capturing at least a portion of a human brain at a predetermined time interval, performing, by the brain disease prediction apparatus, a pre-processing procedure of converting the plurality of test images into test voxels configured to be processed for image analysis, wherein a respective test voxel of the test voxels is data composed of three-dimensional voxel units, mapping, by the brain disease prediction apparatus, first and second test voxels selected from the test voxels acquired from a patient, with each other on a three-dimensional voxel unit, wherein the first test voxel is acquired at a first time-point and the second test voxel is acquired at a second time-point, in which a predetermined time has elapsed from the first time-point, generating, by the brain disease prediction apparatus, a voxel-based data-set based on the mapped first and second test voxels, extracting, by the brain disease prediction apparatus, a change in the test voxels using a deep neural network, and generating, by the brain disease prediction apparatus, a state change probability model based on the change in the test voxels.

According to an exemplary embodiment, a brain disease prediction apparatus for predicting brain disease state change includes a processor, and a memory storing at least one instruction executable by the processor, wherein the at least one instruction is executed by the processor to: acquire a plurality of test images, which comprise images obtained by capturing at least a portion of a human brain at a predetermined time interval, perform a pre-processing procedure of converting the plurality of test images into test voxels configured to be processed for image analysis, wherein a respective test voxel of the test voxels is data composed of three-dimensional voxel units, map first and second test voxels selected from the test voxels acquired from a patient, with each other on a three-dimensional voxel unit, wherein the first test voxel is acquired at a first time-point and a second test voxel is acquired at a second time-point, in which a predetermined time has elapsed from the first time-point, generate a voxel-based data-set based on the mapped first and second test voxels, extract a change in the test voxels using a deep neural network, and generate a state change probability model based on the change in the test voxels.

Other features of the inventive concept are included in the detailed description and drawings.

BRIEF DESCRIPTION OF THE FIGURES

The patent or application file contains at least one drawing executed in color. Copies of this patent or patent application publication with color drawing(s) will be provided by the Office upon request and payment of the necessary fee.

The above and other objects and features will become apparent from the following description with reference to the following figures, wherein like reference numerals refer to like parts throughout the various figures unless otherwise specified, and wherein.

DETAILED DESCRIPTION

Figure 1:
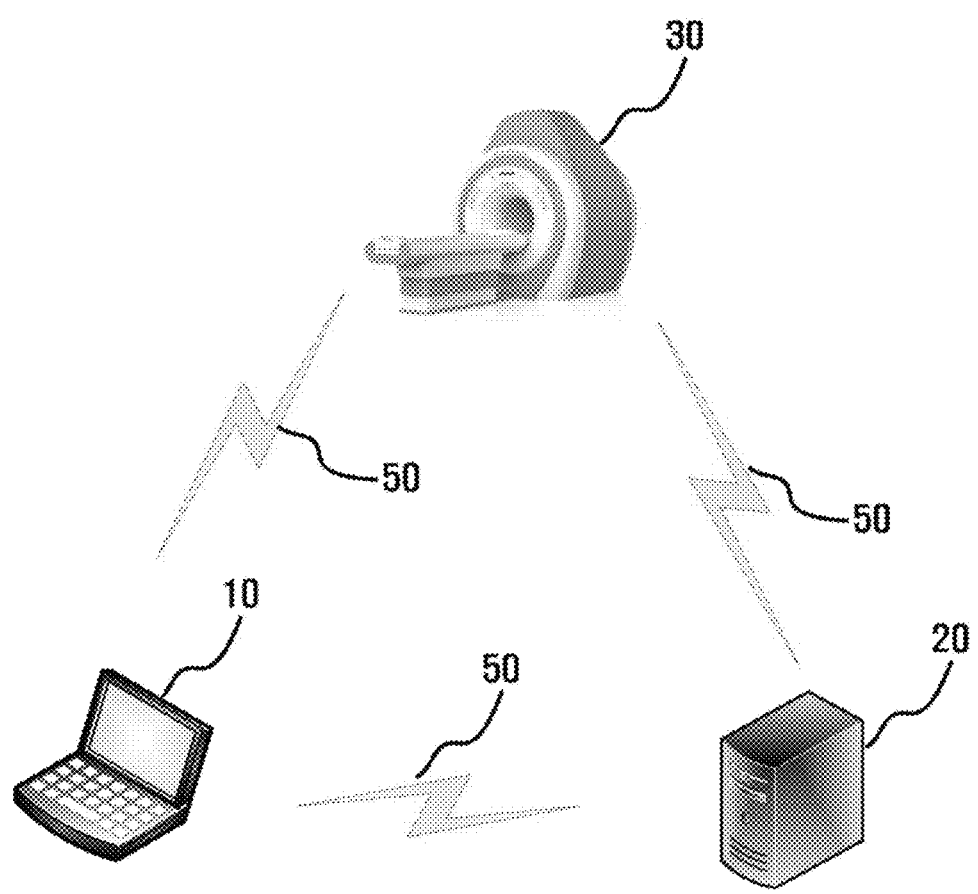
FIG. 1 is a conceptual diagram showing apparatuses for providing a method for predicting a brain disease state change according to some embodiments of the present disclosure.

Advantages and features of the inventive concept, and methods of achieving them will become apparent with reference to embodiments described below in detail in conjunction with the accompanying drawings. However, the inventive concept is not limited to the embodiments disclosed below, but may be implemented in various forms. The present embodiments are provided to merely complete the disclosure of the inventive concept, and to inform merely fully those skilled in the art of the inventive concept of the scope of the inventive concept. The inventive concept is only defined by the scope of the claims.

The terminology used herein is for the purpose of describing the embodiments only and is not intended to limit the inventive concept. As used herein, the singular forms "a" and "an" are intended to include the plural forms as well, unless the context clearly indicates otherwise. It will be further understood that the terms "comprises", "comprising", "includes", and "including" when used in this specification, specify the presence of the stated features, integers, operations, elements, and/or components, but do not preclude the presence or addition of one or more other features, integers, operations, elements, components, and/or portions thereof. Like reference numerals refer to like elements throughout the disclosure. As used herein, the term "and/or" includes any and all combinations of one or more of the associated listed items. Although terms "first", "second", etc. are used to describe various components, it goes without saying that the components are not limited by these terms. These terms are only used to distinguish one component from another component. Therefore, it goes without saying that a first component as mentioned below may be a second component within a technical idea of the inventive concept.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Spatially relative terms "below", "beneath", "lower", "above", "upper", and the like may be used to easily illustrate a correlation between components as shown in the drawings. The spatially relative terms should be understood as terms including an orientation of a component varying in use or operation in addition to an orientation as shown in the drawings. For example, when a drawing is turned over, a first component described as "below" or "beneath" a second component may be placed "above" the second component. Accordingly, the exemplary term "below" may include both "below" and "above". A component may be oriented in a varying direction. Accordingly, the spatially relative terms may be interpreted according to the orientation.

As used herein, a term 'test image' may mean a plurality of images including at least a portion of a human brain captured at a specific time interval.

A first test image may be a base image initially captured for a patient. A second test image may be a follow-up image captured for the same patient after a specific time has elapsed.

A first time-point may mean a time-point at which the first test image is captured. A second time-point may mean a time-point at which the second test image is taken. For example, the first time-point may be an initial measurement time-point, and the second time-point may be 30 minutes after the initial measurement time-point. In another example, the first time-point may mean a time-point before treatment, and the second time-point may mean a time-point after the treatment.

As used herein, a term 'test voxel' may be three-dimensional coordinate information including three-dimensional position-based feature information in a test image acquired from a specific patient. In these embodiments, the feature information may include feature information of a corresponding voxel, feature information of a neighboring voxel thereto, and the like.

As used herein, a term 'first test voxel' may be a test voxel acquired based on the first test image. As used herein, a term 'second test voxel' may be a test voxel acquired based on the second test image.

Hereinafter, embodiments of the inventive concept will be described in detail with reference to the accompanying drawings.

FIG. 1 is a conceptual diagram showing apparatuses for providing a method for predicting a brain disease state change according to some embodiments of the present disclosure.

Referring to FIG. 1, a brain disease prediction system for providing a method for predicting a brain disease state change of the inventive concept includes at least one of a user device 10, a server 20, and a brain disease prediction apparatus 30. The user device 10, the server 20, and the brain disease prediction apparatus 30 are connected to each other over a network 50.

Examples of the user device 10 of the present disclosure include a desktop computer, a laptop computer, a tablet PC, a wireless phone, a mobile phone, a smart phone, a mobile station (MS), a machine-type communication (MTC) device, a M2M (machine-to-machine) device, a D2D (device-to-device) device, user equipment (UE), a wireless device, a wireless terminal (WT), an access terminal (AT), a wireless transmit/receive unit (WTRU), a subscriber station (SS), a subscriber unit (SU), a user terminal (UT), PMP (portable multimedia player), a personal portable terminal (PDA) with wireless communication function, a portable game device with wireless communication function, a navigation device, a digital camera, a DMB (digital multimedia broadcasting) player, a digital audio recorder, a digital audio player, a digital picture recorder, a digital picture player, a digital video recorder, a digital video player, a music storage and playback home appliance with wireless communication function, an internet home appliance capable of wireless internet access and browsing, and portable units or terminals incorporating combinations of the above functions. However, the inventive concept is not limited thereto.

Examples of the server 20 of the present disclosure include a cloud server, an IMS (IP multimedia subsystem) server, a telephony application server, a IM (instant messaging) server, a MGCF (media gateway control function) server, a MSG (messaging gateway) server, a CSCF (call session control function) server. In some embodiments, the server 20 is implemented as an apparatus that refers to an object that transmits and receives data, such as a PC (Personal Computer), a notebook computer, and a tablet PC.

Examples of the brain disease prediction apparatus 30 of the present disclosure include a general computer, an MRI apparatus itself, and a computer connected to the MRI apparatus.

The network 50 of the present disclosure refers to a data communication network for data transmission and reception between the user device 10, the server 20, and the brain disease prediction apparatus 30. A type thereof is not particularly limited.

Examples of the network 50 of the present disclosure include an IP (Internet Protocol) network providing a large data transmission and reception service through the Internet protocol (IP), or include an all IP network that integrates different IP networks.

Herein, in some embodiments, the communication between the user device 10, the server 20, and the brain disease prediction apparatus 30 is established over at least one selected from wireless Internet such as Wi-Fi wireless fidelity, portable Internet such as 802.11x (e.g., 802.11a, 802.11b, 802.11g, 802.11n, 802.11ac), WiBro (wireless broadband internet) or WiMAX (world interoperability for microwave access), a 2G (Second Generation) mobile communication network, such as GSM (global system for mobile communication) or CDMA (code division multiple access), a 3G (Third Generation) mobile communication network, such as WCDMA (wideband code division multiple access) or CDMA2000, a 3.5G mobile communication network, such as HSDPA (high speed downlink packet access) or HSUPA (high speed uplink packet access), a 4G (Fourth Generation) mobile communication network, such as LTE (long term evolution network) or LTE-Advanced (LTE-A) network, 5G (Fifth Generation) mobile communication network, UWB (Ultra-Wide Band), Bluetooth, Zigbee, a satellite communication network, and combinations thereof.

Figure 2:
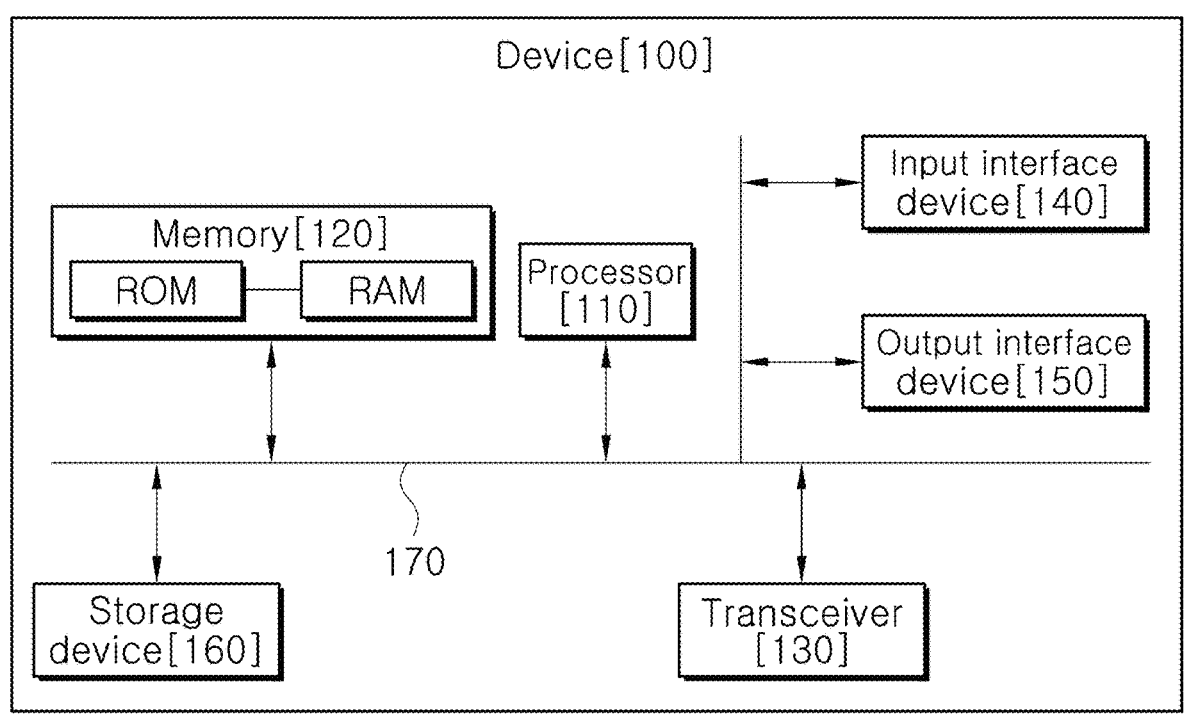
FIG. 2 is a block diagram showing a configuration of a device configured to perform a method for predicting brain disease state change according to some embodiments of the present disclosure.

FIG. 2 is a block diagram showing a configuration of a device configured to perform a method for predicting brain disease state change according to some embodiments of the present disclosure.

Referring to FIG. 2, a device 100 in some embodiments is the user device 10, and the device 100 in some other embodiments is the server 20. That is, the device 100 is a device configured to perform a method for predicting brain disease state change according to some embodiments of the present disclosure. The device 100 in some embodiments includes at least one processor 110, a memory 120, and a transceiver 130 connected to the network 50 to perform communication. Moreover, the device 100 in some embodiments further includes an input interface device 140, an output interface device 150, a storage device 160, and the like. The components included in the device 100 in some embodiments is connected to each other via a bus 170 and communicates with each other.

The output interface device 150 in some embodiments is a display. In these embodiments, the display displays and outputs information processed by the user device 10. Specifically, the display in some embodiments displays access information required for wired/wireless connection, advertisement information, or access information re-entry request command using a UI (user interface) or a GUI (graphic user interface).

Further, the display in some embodiments includes at least one of a liquid crystal display, a thin film transistor-liquid crystal display, an organic light-emitting diode, a flexible display, and a 3D display. The display in some embodiments includes two or more thereof depending on implementations. For example, an external display and an internal display in some embodiments are simultaneously provided in the user device 10.

The processor 110 in some embodiments executes a program command stored in at least one of the memory 120 and the storage device 160. The processor 110 in some embodiments includes a central processing unit (CPU), a graphics processing unit (GPU), or a dedicated processor in which methods according to some embodiments of the present disclosure are performed. Each of the memory 120 and the storage device 160 in some embodiments is embodied as at least one of volatile storage medium and non-volatile storage medium (i.e., non-transitory storage medium). For example, the memory 120 in some embodiments includes at least one of a read only memory (ROM), and a random access memory (RAM).

Figure 3:
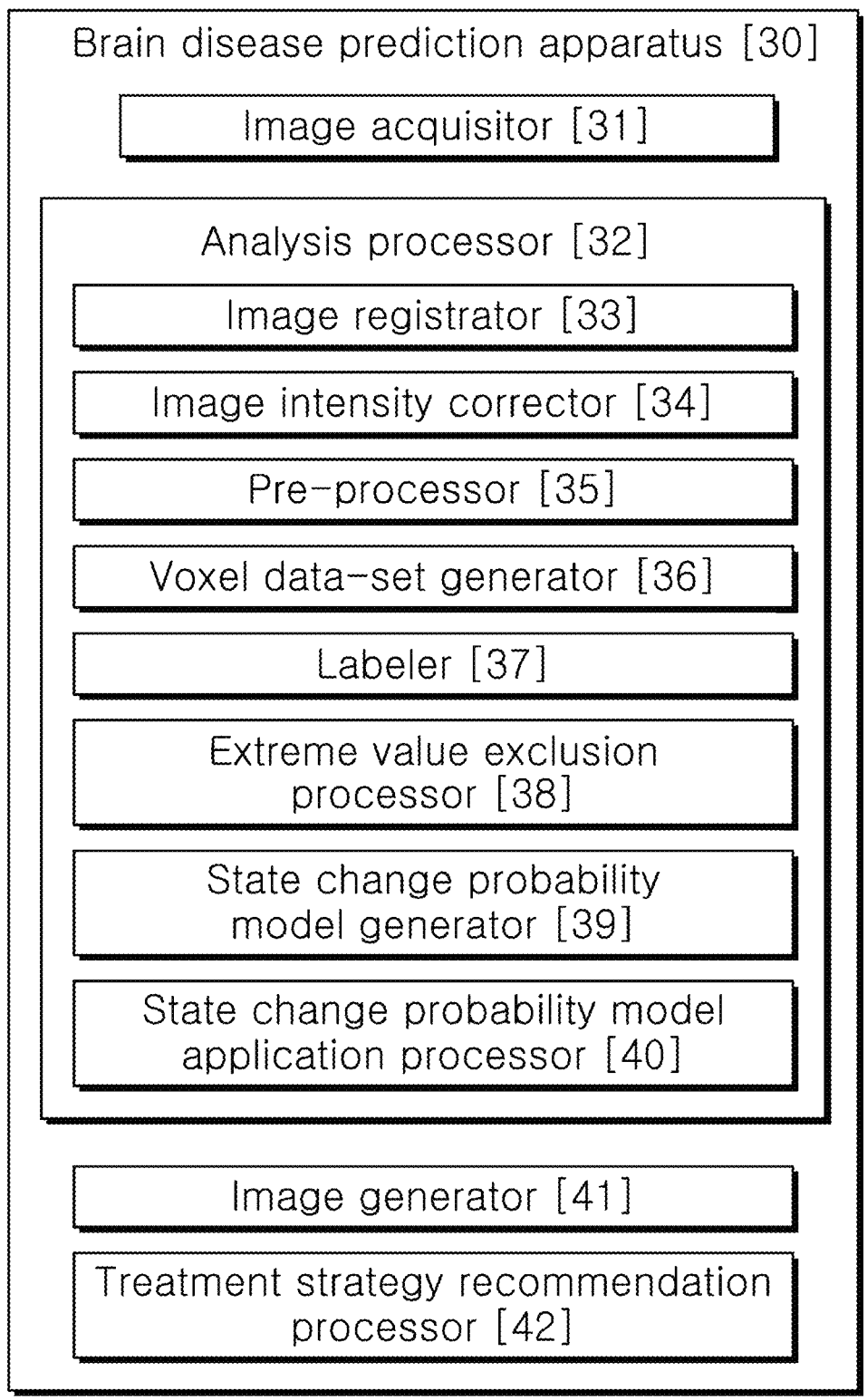
FIG. 3 is a block diagram showing a configuration of a brain disease prediction apparatus according to some embodiments of the present disclosure.

FIG. 3 is a block diagram showing a configuration of a brain disease prediction apparatus according to some embodiments of the present disclosure.

Referring to FIG. 3, the brain disease prediction apparatus 30 according to some embodiments of the present disclosure includes at least one of an image acquisitor 31, an analysis processor 32, an image generator 41, and a treatment strategy recommendation processor 42. The analysis processor 32 includes at least one of an image registrator 33, an image intensity corrector 34, a pre-processor 35, a voxel data-set generator 36, a labeler 37, an extreme value exclusion processor 38, a state change probability model generator 39, and a state change probability model application processor 40.

The image acquisitor 31 in some embodiments images a plurality of test images captured for a portion of a human brain.

In some embodiments, the image acquisitor 31 acquires a plurality of captured images by capturing a plurality of images including at least a portion of the human brain. Alternatively, the image acquisitor 31 acquire a plurality of captured images by externally receiving a plurality of pre-captured images including at least a portion of the human brain.

In these embodiments, the test images are images captured at a specific time interval. For example, the test images are images captured at a time interval of 30 seconds, 1 minute, 5 minutes, or 10 minutes.

The analysis processor 32 in some embodiments performs a process of predicting brain disease state change based on the captured test images or the test images as externally received. Image registration and image intensity correction are portions of a pre-processing procedure. In these embodiments, the pre-processing is for converting the test images into data to be processed for image analysis.

The image registrator 33 included in the analysis processor 32 performs image registration between tests images of the same time-point or image registration between test images of different time-points.

Image registration in some embodiments is registering a test image based on a standard brain image. In these embodiments, the standard brain image refers to a standard brain shape defined based on physical conditions such as a height, a body weight, and a gender.

The image acquisitor 31 in some embodiments collects images related to the human brain captured at various angles. The collected images of the human brain configured to be integrated into one three-dimensional brain image. Accordingly, the image registrator 33 registers the plurality of the collected images of the human brain based on the standard brain image.

The image registrator 33 in some embodiments performs image registration between tests images of the same time-point or image registration between test images of different time-points. The image registrator 33 in some embodiments registers a plurality of images captured at different time-points based on a specific patient among a plurality of brain disease patients. When registering the plurality of images captured at different time-points, change in the brain disease for each patient is checked.

The image registrator 33 in some embodiments improves registration performance by excluding brain lesion regions and cerebral hemorrhage regions from a registration target during the registration process. That is, the image registrator 33 performs registration between various images acquired at an initial diagnosis time-point.

The image intensity corrector 34 in some embodiments corrects an intensity of an image captured using an Magnetic resonance imaging (MRI) apparatus. In some embodiments of the pre-treatment, the brain disease prediction apparatus 30 performs the pre-processing based on a brightness (or intensity) of the capture image compared to that of a normal tissue in DWI (diffusion weighted image).

However, the MRI image captured using the MRI apparatus does not have a reference image intensity, which is not the case in a CT image. Thus, the image intensity in a brain lesion varies depending on varying MRI apparatus and parameters. To solve this problem, the brain disease prediction apparatus 30 in some embodiments corrects the intensity based on a GMM (Gaussian-Mixture Model).

The image registrator 33 in some embodiments performs image registration based on image intensities of a plurality of images whose intensities are corrected through the GMM. A conceptual diagram showing the pre-processing of the image using the Gaussian mixture model (GMM) is described in FIG. 7.

The voxel data-set generator 36 in some embodiments maps the first test voxel acquired based on the first test image and the second test voxel acquired based on the second test image among test voxels acquired from a specific patient with each other on a three-dimensional voxel unit to generate a voxel-based data-set.

The labeler 37 in some embodiments labels, with an identifiable mark, a portion of the test image into which a stroke would spread.

The extreme value exclusion processor 38 in some embodiments excludes, at a predetermined percentage, among measurement values, one or more measurement values having a greater state change rate than a first threshold state change rate, and one of more measurement values having a lower state change rate than a second threshold state change rate, in a process of generating of a state change probability model.

Moreover, the extreme value exclusion processor 38 in some embodiments excludes an extreme value indicating a value whose state change rate is above or below a predetermined rate threshold, as above.

The state change probability model generator 39 in some embodiments extracts a change in the test voxels using a deep neural network, and generates the state change probability model based on the change in the test voxels.

The state change probability model application processor 40 in some embodiments applies the state change probability model to the stroke image acquired from a patient. The state change probability model application processor 40 in some embodiments calculates information about how a patient's stroke progresses or what happens when a treatment thereof is performed, based on a patient's stroke image.

The image generator 41 in some embodiments generates a prediction image visualizing the probability model in a three-dimensional manner. The prediction image in some embodiments is visual information on how a patient's stroke progresses or what happens when a treatment thereof is performed.

The transceiver in some embodiments transmits the generated prediction image to the user device 10.

The brain disease prediction apparatus 30 in some embodiments transmits the prediction image to the user device 10, and further provides visual or audible information about the prediction image by itself.

The treatment strategy recommendation processor 42 in some embodiments derives at least one of a treatment timing and a treatment strategy based on the prediction image.

In such amendments, one or more test images are generated to be used for deriving at least one of the treatment timing and the treatment strategy. Those test images includes at least one or more of a prediction image in a situation of performing no treatment, a prediction image in a situation of preforming a drug treatment only, and a prediction image of performing a variety of types of available treatments more than a mere drug treatment, which are described below, and a prediction image of performing all types of available treatments including a drug treatment and other treatments more than a mere drug treatment, which are described below. Accordingly, a variety of test images can be generated, and various state change probability values of voxels would be acquired.

The above various state change probability values would be compared to derive at least one of the treatment timing and the treatment strategy. For example, a state change probability of a particular voxel of each image is calculated, and the calculated state change probability per a voxel are compared with each other, and a sum of differences of the compared state change probabilities is used for deriving at least one of the treatment timing and the treatment strategy. In some embodiments, the particular voxel is a voxel related to a brain disease.

The transceiver in some embodiments transmit at least one of the treatment timing and the treatment strategy to the user device 10.

The brain disease prediction apparatus 30 in some embodiments transmits at least one of the treatment timing and the treatment strategy to the user device 10 and further provides at least one of the treatment timing and the treatment strategy visually or audibly by itself.

Figure 4:
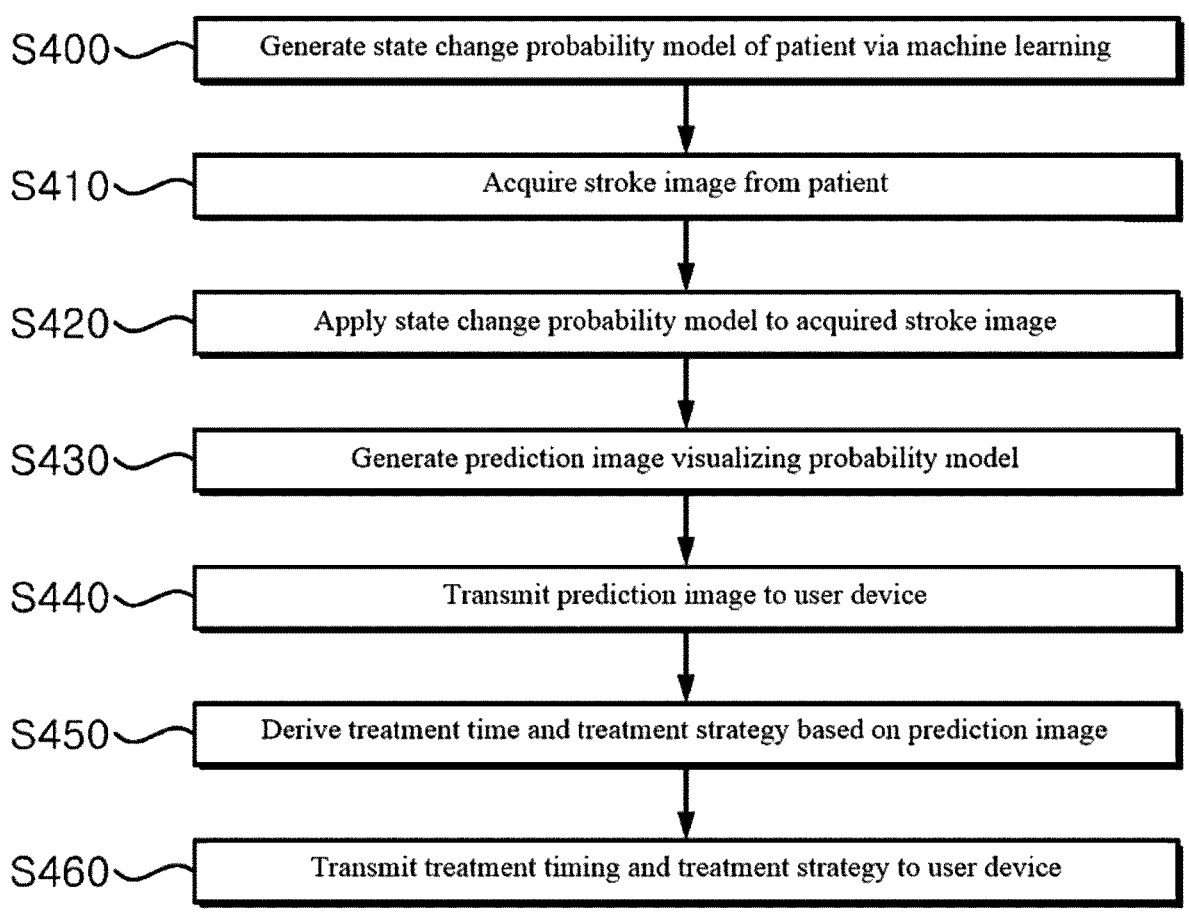
FIG. 4 is a flowchart illustrating a method for predicting brain disease state change according to some embodiments of the present disclosure.

FIG. 4 is a flowchart showing a method for predicting brain disease state change according to some embodiments of the present disclosure.

Referring to FIG. 4, the brain disease prediction apparatus 30 in some embodiments generates the state change probability model of the patient via machine learning (S400). The brain disease prediction apparatus 30 in some embodiments acquires a stroke image as a brain image including a stroke from a patient (S410). The brain disease prediction apparatus 30 in some embodiments applies the state change probability model to the acquired stroke image (S420).

The brain disease prediction apparatus 30 in some embodiments generates the prediction image visualizing the probability model in the three-dimensional manner (S430). The prediction image in some embodiments is visual information indicating how a patient's stroke progresses or what happens when a treatment thereof is performed, based on the stroke image of the patient.

Specifically, the brain disease prediction apparatus 30 in some embodiments determines a time-point at which the state change probability model is applied as a reference time-point. When there is no special action for the brain disease, the brain disease prediction apparatus 30 generates the prediction image after a specific time has elapsed from the reference time-point Moreover, when performing treatment for the brain disease, the brain disease prediction apparatus 30 in some embodiments generates the prediction image after a specific time has elapsed from the reference time-point based on each treatment strategy.

In these embodiments, the treatment strategy includes one or more selected from the group consisting of treatment of an acute stage, and treatment of cerebral parenchyma bleeding. Specifically, the treatment strategies includes general preservation treatment, intravenous thrombolysis, intra-arterial thrombolysis, decompression surgery of malignant middle cerebral artery infarction, drug treatment of cerebral parenchyma bleeding, brain pressure control, medical treatment of cerebral parenchyma bleeding associated with anti-coagulants, treatment of non-cardiogenic embolic stroke, anti-thrombotic agent based treatment of non-cardiogenic transient cerebral ischemia, treatment of cardiogenic embolic stroke, anti-thrombotic agent based treatment of cardiogenic transient cerebral ischemia, and surgery of cerebrovascular stenosis-occlusive disease. However, the present disclosure is not limited thereto.

The brain disease prediction apparatus 30 in some embodiments transmits the prediction image to the user device 10 (S440). The user device 10 in some embodiments receives the prediction image from the brain disease prediction apparatus 30.

The brain disease prediction apparatus 30 in some embodiments derives at least one of the treatment timing and the treatment strategy based on the prediction image (S450). Specifically, the brain disease prediction apparatus 30 in some embodiments determines an optimal treatment strategy based on comparison results between prediction images after a specific time has elapsed, for each treatment strategy. For example, the brain disease prediction apparatus generates an after-treatment prediction image for each treatment timing, compares the generated after-treatment prediction images for a plurality of treatment timings to determine an optimal after-treatment prediction image, and determine a treatment timing corresponding to the determined optimal after-treatment prediction image as an optimal treatment timing. For another example, the brain disease prediction apparatus generates an after-treatment prediction image for each treatment strategy, compares the generated after-treatment prediction images for a plurality of treatment strategies to determine an optimal after-treatment prediction image, and determine a treatment strategy corresponding to the determined optimal after-treatment prediction image as an optimal treatment strategy.

The brain disease prediction apparatus 30 in some embodiments transmits at least one of the treatment timing and the treatment strategy obtained via the comparison result of the prediction images, to the user device 10 (S460).

The brain disease prediction apparatus 30 in some embodiments transmits at least one of the treatment timing and the treatment strategy to the user device 10 and further provides at least one of the treatment timing and the treatment strategy visually or audibly by itself.

Figure 5:
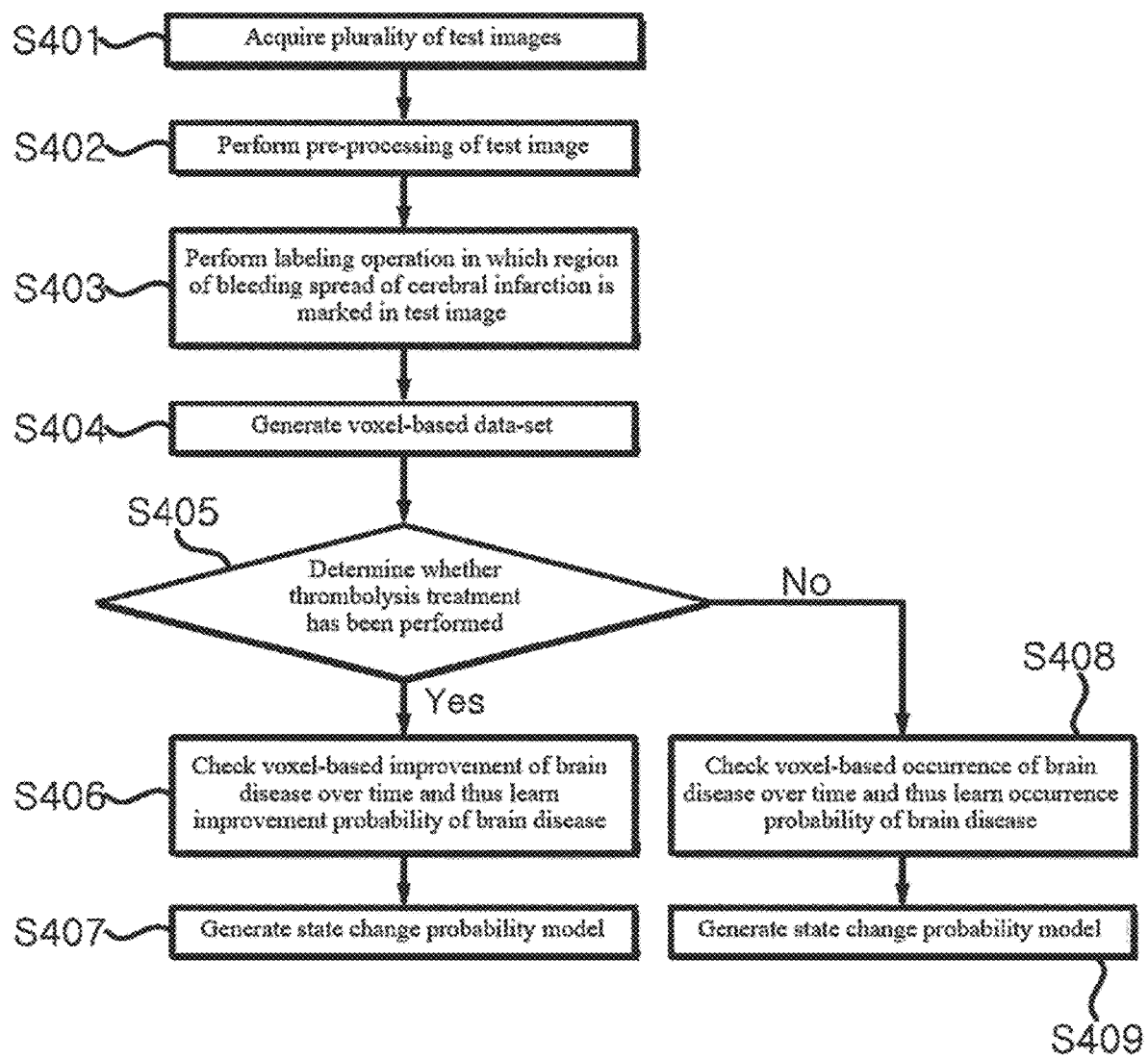
FIG. 5 is a flowchart showing a state change probability model generation method according to some embodiments of the present disclosure.

FIG. 5 is a flowchart showing a state change probability model generation method according to some embodiments of the present disclosure.

Referring to FIG. 5, a practical embodiment of S400 for generating the state change probability model as disclosed in FIG. 4 is shown.

The brain disease prediction apparatus 30 in some embodiments acquires a plurality of test images (S401). In these embodiments, the test images are taken via the MRI apparatus. Alternatively, the test image are images acquired from an outside (i.e., received from an external device). In these embodiments, the images acquired from the outside are images captured via another MRI apparatus or images captured via another type of an imaging apparatus. The brain disease prediction apparatus 30 in some embodiments acquires the test image in a wired or wireless manner from the outside.

The brain disease prediction apparatus 30 in some embodiments performs pre-processing of converting the test images into test voxels configured to be processed for image analysis (S402). The pre-processing procedure performed by the brain disease prediction apparatus 30 in some embodiments includes at least one of image intensity correction, image registration, and conversion of the images to the test voxels.

The brain disease prediction apparatus 30 in some embodiments corrects the intensity of the image captured via the MRI apparatus. In one embodiment of the pre-treatment, the brain disease prediction apparatus 30 performs the pre-processing based on a brightness (or intensity) of the capture image compared to that of a normal tissue in DWI (diffusion weighted image).

However, the MRI image captured using the MRI apparatus does not have a reference image intensity, which is not the case in a CT image. Thus, the image intensity in a brain lesion varies depending on varying MRI apparatus and parameters. To solve this problem, the brain disease prediction apparatus 30 in some embodiments corrects the intensity based on the GMM (Gaussian-Mixture Model).

The brain disease prediction apparatus 30 in some embodiments improves registration performance by excluding brain lesion regions and cerebral hemorrhage regions from a registration target during the registration process. That is, the brain disease prediction apparatus 30 in some embodiments performs registration between various images acquired at an initial diagnosis time-point.

Figure 7:
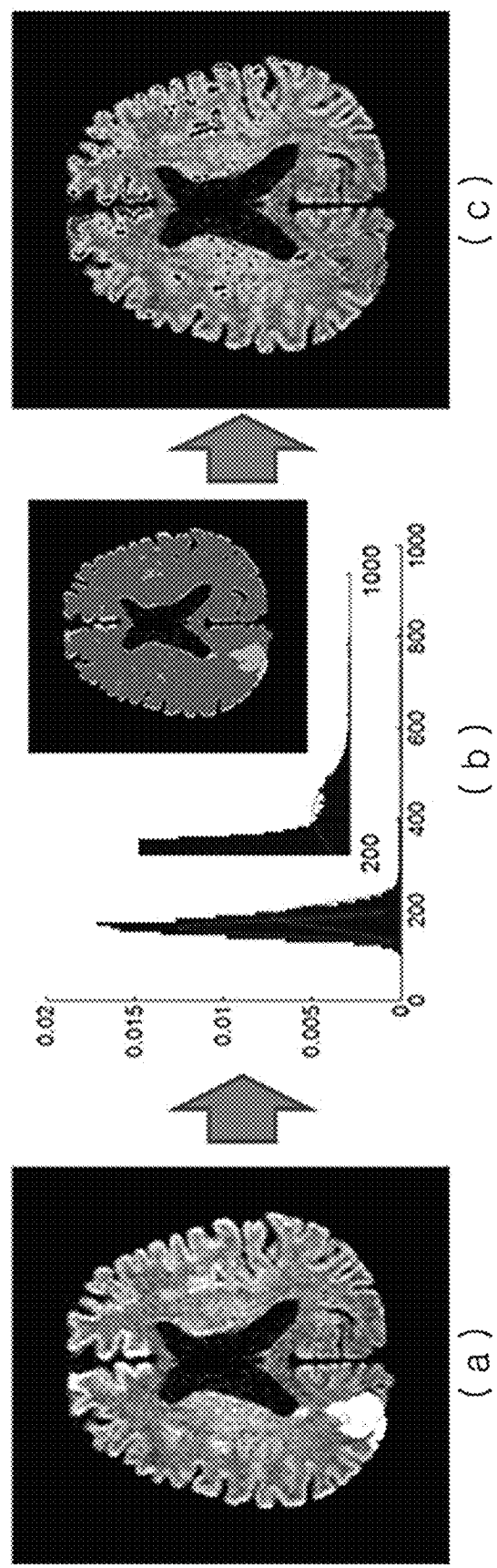
FIG. 7 is a conceptual diagram showing a pre-processing process according to some embodiments of the present disclosure.

The brain disease prediction apparatus 30 in some embodiments performs image registration based on image intensities of a plurality of images whose intensities are corrected through the GMM. A conceptual diagram showing the pre-processing of the image using the Gaussian mixture model (GMM) is shown in FIG. 7.

The brain disease prediction apparatus 30 in some embodiments performs a labeling operation in which a region of bleeding spread of the cerebral infarction (or brain lesion) is marked in the test image (S403). In these embodiments, the region of the bleeding spread of the cerebral infarction refers to a region to which the stroke is expected to spread.

The brain disease prediction apparatus 30 in some embodiments maps the first test voxel acquired based on the first test image and the second test voxel acquired based on the second test image among the voxels acquired from a specific patient with each other on a three-dimensional voxel units, thereby to generate the voxel-based data-set (S404).

Specifically, the brain disease prediction apparatus 30 in some embodiments compares first feature information obtained from the first test voxel in the first test image acquired at the first time-point and second feature information acquired from the second test voxel in the second test image acquired at the second time-point with each other and performs machine learning of the comparison result, together with considering a time duration elapsed from the first time-point to the second time-point.

In these embodiments, the test voxel includes one state information among "normal", "cerebral infarction", "cerebral hemorrhage". The change in the test voxel means a change from one state among the normal, cerebral infarction, and cerebral hemorrhage states to another state among them. For example, the test voxel in some embodiments includes information indicating that a state of a first position (a position of a specific voxel) of a brain at the first time-point is "normal" and then a state of the first position of the brain at the second time-point is "cerebral infarction", and then a state of the first position of the brain at a third time-point is "cerebral hemorrhage". In these embodiments, the state of the first position of the brain has changed over time. The change in the state of the position of the specific voxel refers to the change in the test voxels.

A state of the test voxel in some embodiments changes from "normal" to "cerebral infarction", and from "cerebral infarction" to "cerebral hemorrhage", and "normal" to "cerebral hemorrhage" over time when there is no separate treatment thereof. Moreover, the state of the test voxel in some embodiments changes from "cerebral infarction" to "normal" and from "cerebral hemorrhage" to "normal" over time when thrombolytic treatment is performed.

The brain disease prediction apparatus 30 in some embodiments determines whether the thrombolysis treatment has been performed (S405). When the brain disease prediction apparatus 30 determines that the thrombolysis treatment has been performed, the brain disease prediction apparatus 30 checks voxel-based improvement of the brain disease, based on the voxel-based data-set, over time and thus learn an improvement probability of the brain disease (S406). In these embodiments, the brain disease improvement probability refers to a probability about whether the brain disease is improved based on each voxel when the thrombolysis treatment is performed at a specific time-point. The brain disease prediction apparatus 30 in some embodiments generates the state change probability model based on each voxel-based brain disease improvement probability (S407).

In another embodiment of the present disclosure, the brain disease prediction apparatus 30 generates the state change probability model based on the change in the test voxel according to various treatment schemes. Specifically, in machine learning the improvement probability of the disease according to various treatment schemes, the first test voxel may be a voxel prior to performing the treatment. The second test voxel may be a voxel when a certain time has lapsed after performing the treatment. The brain disease prediction apparatus 30 may learn the improvement probability based on the change of the test voxel before and after the treatment and thus generates the probability model according to a specific treatment scheme.

When the brain disease prediction apparatus 30 determines that the thrombolysis has not been conducted, the brain disease prediction apparatus 30 checks voxel-based occurrence of the brain disease based on the voxel-based data-set over time and thus may learn an occurrence probability of the brain disease (S408). In these embodiments, the brain disease occurrence probability refers to a probability about how much the brain disease has developed for each voxel based on a stroke occurrence level at a specific time-point. The brain disease prediction apparatus 30 generates the state change probability model based on each voxel-based brain disease occurrence probability (S409).

In another embodiment of the present disclosure, the state change probability model is generated in consideration of at least one of age of a patient, presence or absence of atrial fibrillation of a patient, presence or absence of hypertension of a patient, presence or absence of hyperlipidemia of a patient, drinking experience of a patient, smoking experience of a patient, and presence or absence of diabetes of a patient.

For example, a rate of change of the test voxel of patients of high blood pressure may be faster than that of normal blood pressure patients. Therefore, when the state change probability model extracted from hypertensive patients may be applied to other hypertensive patients, the model may act as a relatively more accurate prediction model.

Figure 6:
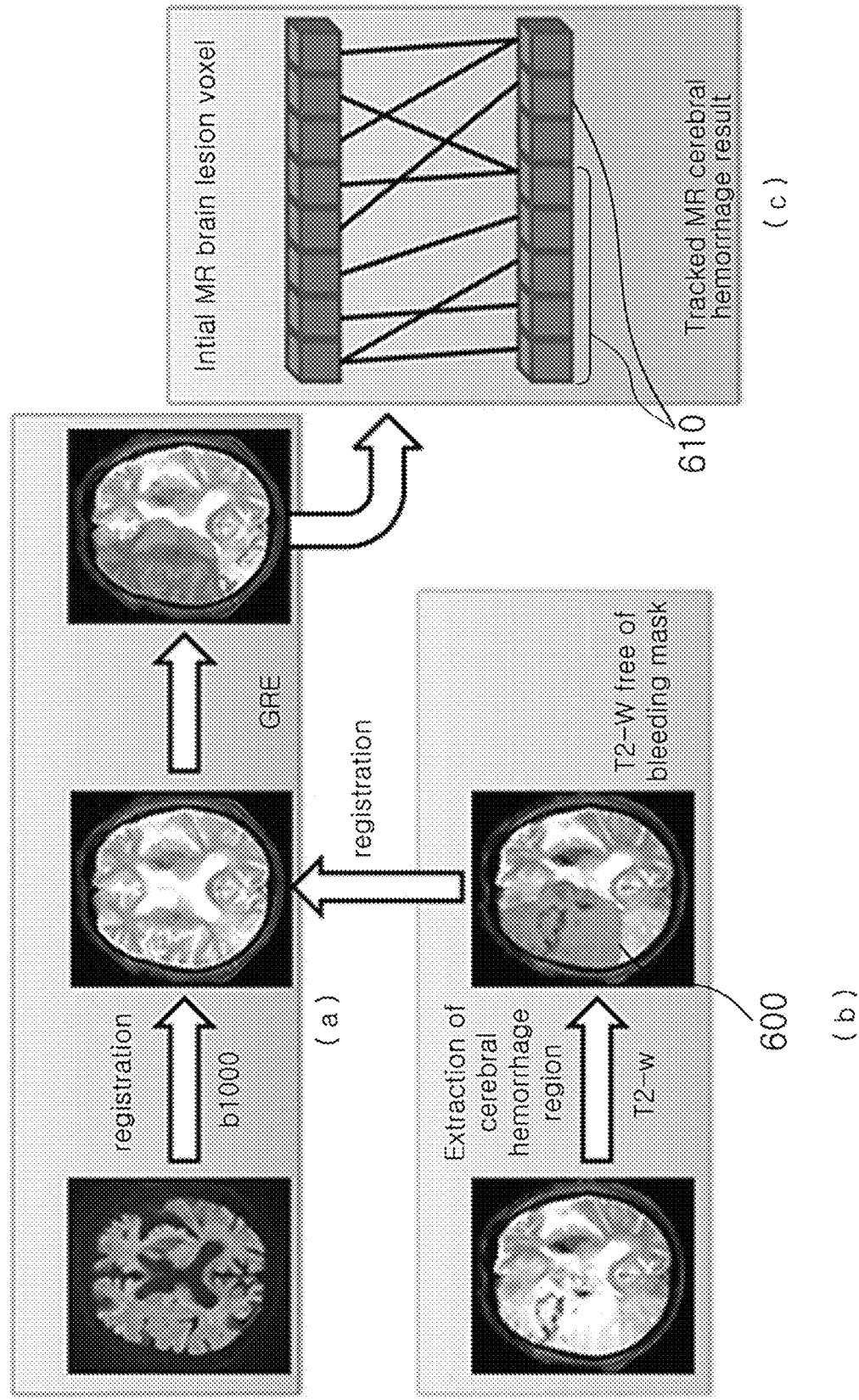
FIG. 6 is a conceptual diagram showing registration of an image according to some embodiments of the present disclosure.

FIG. 6 is a conceptual diagram showing registration of an image according to some embodiments of the present disclosure.

Referring to FIG. 6, (a) of FIG. 6 is an MRI image measured at the first time-point. (b) of FIG. 6 is an MRI image measured at the second time-point. (c) of FIG. 6 is a diagram of a mapping between a voxel value of the MRI image measured at the first time-point and a voxel value of the MRI image measured at the second time-point.

Specifically, referring to the image of (a) of FIG. 6, the brain disease prediction apparatus 30 in some embodiments acquires the first test voxel by pre-processing the MRI image measured at the first time-point. In these embodiments, a first part displayed on a left side of the first brain image is a cerebral infarction voxel. A second part displayed on a left side of the third image is that the cerebral infarction voxel and the cerebral hemorrhage voxel are present simultaneously.

Referring to (b) of FIG. 6, the brain disease prediction apparatus 30 in some embodiments acquires the second test voxel by pre-processing the MRI image measured at the second time-point. In these embodiments, a third part displayed on the left side of the second brain image is an identifier 600 indicating a cerebral hemorrhage voxel. Referring to the image of (b) of FIG. 6 as measured after a predetermined time has lapsed from the first time-point, the cerebral hemorrhage occurred in the left hemisphere.

When registering the image in (a) of FIG. 6 and the image in (b) of FIG. 6 with each other to correspond voxel values thereof with each other, the brain disease prediction apparatus 30 maps the first test voxel and the second test voxel with each other on a voxel unit to generate the voxel-based data-set.

A voxel expressed at a top of the image in (c) of FIG. 6 means an initial MRI brain lesion voxel measured at the first time-point. A voxel expressed at a bottom thereof may mean a tracked MRI brain lesion voxel measured at the second time-point. A block 610 shown at the bottom of the image in (c) of FIG. 6 may mean a cerebral hemorrhage voxel.

The brain disease prediction apparatus 30 in some embodiments generates a data-set regarding an influencing range on a voxel basis. In these embodiments, a specific cerebral infarction voxel imparts cerebral hemorrhage effect to a neighboring voxel spaced from the specific cerebral infarction voxel by the influencing range. The brain disease prediction apparatus 30 in some embodiments applies this data-set to a machine learning algorithm based on the deep neural network to generate the state change probability model.

FIG. 7 is a conceptual diagram showing a pre-processing process according to some embodiments of the present disclosure.

Referring to FIG. 7, the brain disease prediction apparatus 30 in some embodiments uses a GRE (Gradient Recalled Echo) MRI image as an example of an image to be used for the labeling operation in which a region of a bleeding spread of a stroke is marked in in a stroke image captured at the second time-point.

FIG. 7 is a measurement image of an extracted brain disease region subjected to a GMM-based DWI image correction process as analyzed via pre-experimentation.

Figure 8A:
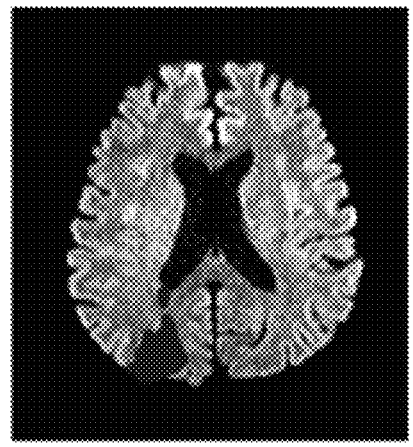
FIGS. 8A, 8B, and 8C are conceptual diagrams showing a pre-processing result according to some embodiments of the present disclosure.
Figure 8B:
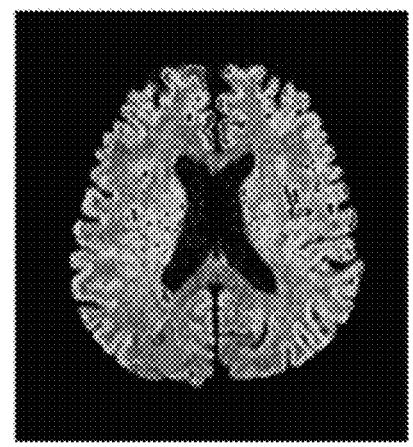
Figure 8C:
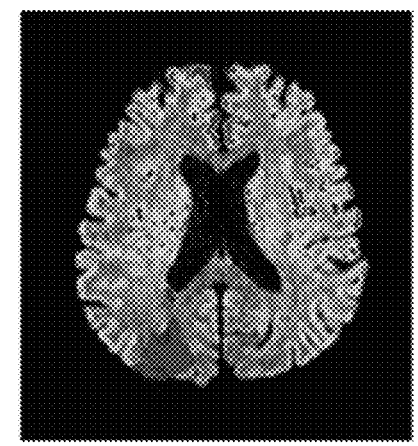

FIGS. 8A, 8B, and 8C are conceptual diagrams showing a pre-processing result value according to some embodiments of the present disclosure.

FIG. 8A is an image of a lesion as manually drawn by a specialist, FIG. 8B is an image of a lesion as automatically extracted based on the GMM, for the brain lesion of the same patient, and FIG. 8C is an overlapping image therebetween for comparison. A part corresponding to the lesion may refer to a lower left portion of each image.

Figure 9:
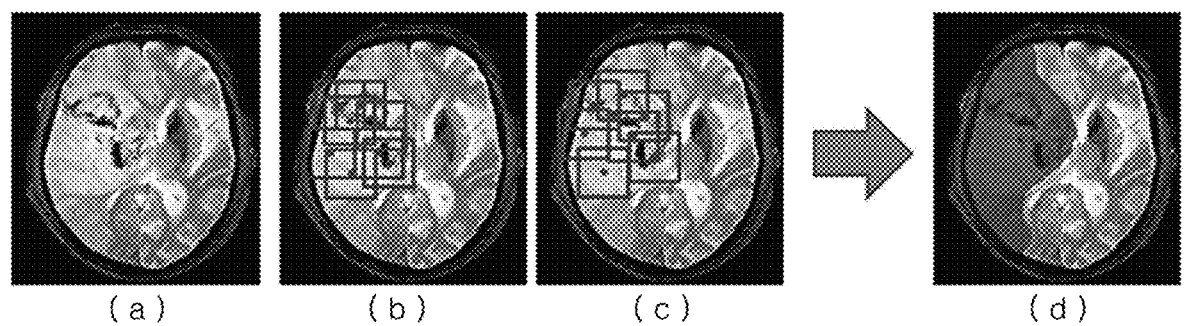
FIG. 9 is a conceptual diagram showing a labeling process according to some embodiments of the present disclosure.

FIG. 9 is a conceptual diagram showing a labeling process according to some embodiments of the present disclosure.

Referring to FIG. 9, the brain disease prediction apparatus 30 in some embodiments learns data on a voxel basis. For convenience of labeling in the tracked image, the user may click a number of small rectangles on a bleeding spread position instead of drawing an accurate bleeding spread mask.

In this way, a user trains the machine learning algorithm in a supervised manner such that the machine learning algorithm recognizes that the bleeding will spread to a region corresponding to the rectangle. The cerebral hemorrhage region may be labeled by a large number of stroke specialists, such that a region with high reliability among evaluators may be set as the bleeding spread region. The bleeding spread region may be expressed in a binary manner (0: no bleeding or 1: bleeding).

Figure 10:
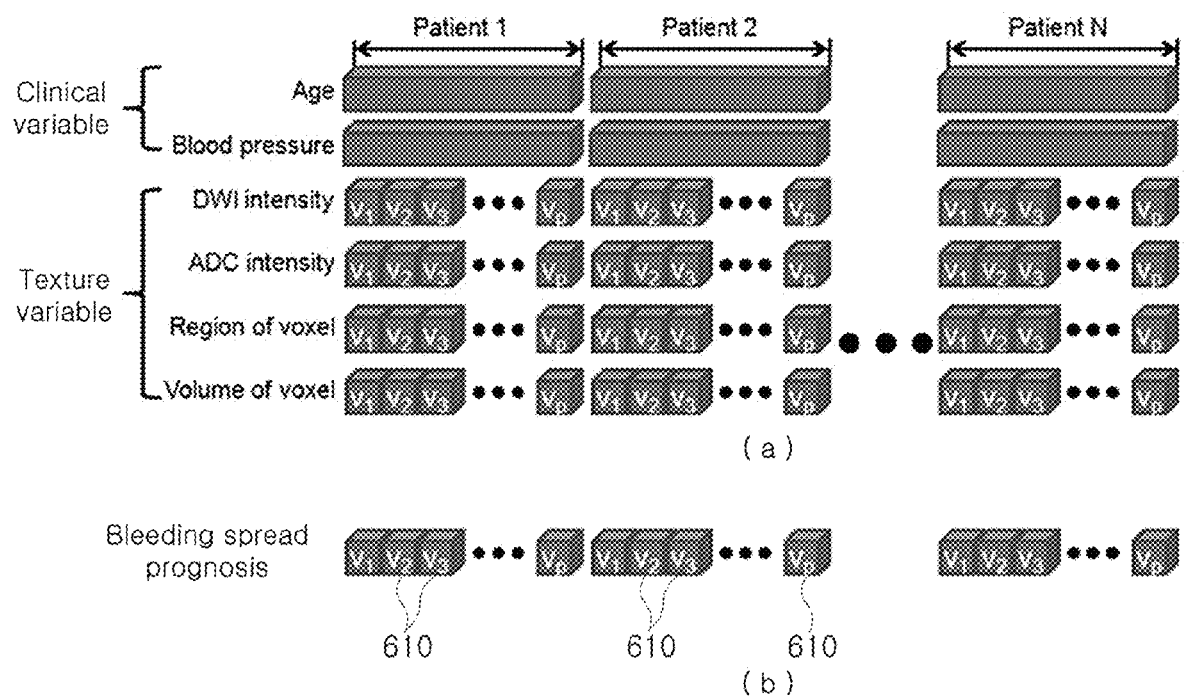
FIG. 10 is a conceptual diagram showing modeling variables according to some embodiments of the present disclosure.

FIG. 10 is a conceptual diagram showing modeling variables according to some embodiments of the present disclosure.

Referring to FIG. 10, voxel information may be determined based on image variables extracted from various MRI image values (e.g., Apparent diffusion coefficient (ADC), diffusion-weighted imaging (DWI), Gradient echo sequences (GRE), Fluid attenuation inversion recovery (FLAIR), and perfusion-weighted imaging (PWI)).

In this case, a set of variables including a texture variable (volume/mass/brain region) of the brain disease to which the voxel belongs, and a patient's clinical variable (e.g., age and blood pressure) may be used for probability modeling.

An observation of data used for learning the probability model may be defined as the number of brain lesion voxels per patient. An input variable (feature) may have a voxel-based image/clinical variable. That is, according to the technical feature of the present disclosure, the state change probability model may be created based on the voxel-based data-set rather than a patient-based data-set. The block 610 shown in the image (b) of FIG. 10 may mean a cerebral hemorrhage voxel.

Figure 11:
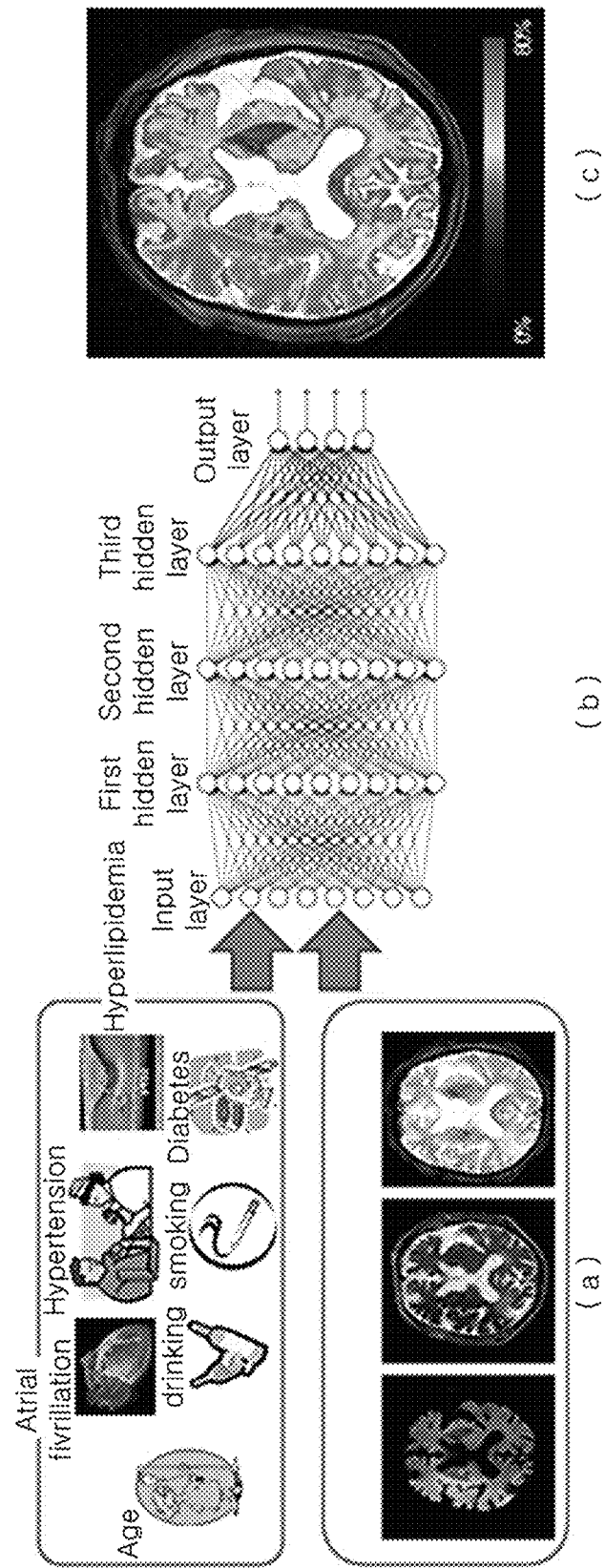
FIG. 11 is a conceptual diagram showing a method for predicting brain disease state change according to some embodiments of the present disclosure.

FIG. 11 is a conceptual diagram showing a method for predicting brain disease state change according to some embodiments of the present disclosure.

Referring to FIG. 11, (a) of FIG. 11 is a diagram indicating that the state change probability model is created in consideration of at least one of age of a patient, presence or absence of atrial fibrillation of a patient, presence or absence of hypertension of a patient, presence or absence of hyperlipidemia of a patient, drinking experience of a patient, smoking experience of a patient, or presence or absence of diabetes of a patient.

(b) of FIG. 11 is a diagram showing a process in which the brain disease prediction apparatus 30 maps the first test voxel obtained based on the first test image and the second test voxel obtained based on the second test image among the test voxels obtained from a specific patient with each other on a voxel basis to generate the voxel-based data-set.

(c) of FIG. 11 is a diagram illustrating a process in which the actual brain image of the patient is applied to the generated state change probability model to create the prediction image in which the probability model is visualized in the three-dimensional manner. The prediction image may be visual information for predicting how the stroke of the patient progresses or what will happen when the treatment is performed, based on the stroke image of the patient.

Figure 12:
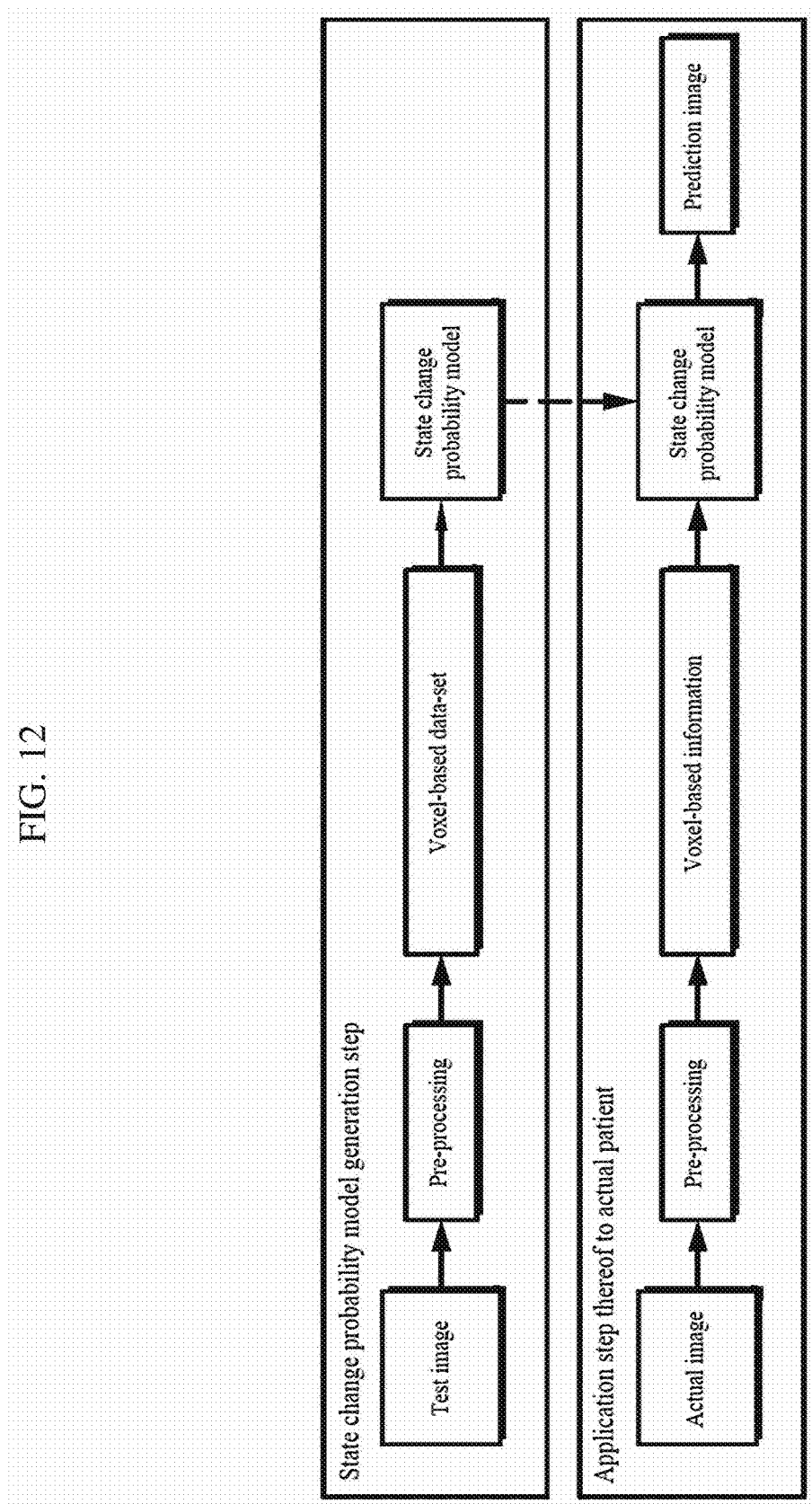
FIG. 12 is a block diagram showing a process of a method for predicting brain disease state change according to some embodiments of the present disclosure.

FIG. 12 is a block diagram showing a process of a method for predicting brain disease state change according to some embodiments of the present disclosure.

Referring to FIG. 12, an upper box represents a state change probability model generation step, and a lower box represents an application step thereof to an actual patient. The state change probability model is generated via the process of generating the voxel-based data-set by preprocessing the test image, and then generating the state change probability model based on the voxel-based data-set.

The application step to the actual patient may be performed by pre-processing an actual image to acquire voxel-based information and applying the voxel-based information to the acquired state change probability model to acquire the prediction image.

The deep neural network (DNN) according to some embodiments of the present disclosure means a system or network that builds at least one layer in at least one computer and performs determinations based on a plurality of data. For example, the DNN may be implemented as a set of layers including a convolutional pooling layer, a locally-connected layer, and a fully-connected layer. The convolutional pooling layer or the locally-connected layer may be configured to extract features in an image. The fully-connected layer may determine a correlation between the features of the image. In some embodiments, an overall structure of the DNN may be constructed such that the convolutional pooling layer is connected to the locally-connected layer which in turn is connected to the fully-connected layer. The DNN may include various determination criteria, that is, parameters, and may add new determination criteria, that is, new parameters, via analysis of an input image.

The DNN according to some embodiments of the present disclosure has a structure referred to as a convolutional neural network suitable for prediction of a state change of a lung disease. The DNN has a structure in which a feature extraction layer that autonomously learns a feature with the greatest discriminative power from given image data is integrated with a prediction layer that learns a prediction model to produce the highest prediction performance based on the extracted feature.

The feature extraction layer has a structure in which a convolution layer for applying a plurality of filters to each region of the image to create a feature map, and a pooling layer for pooling feature maps spatially to extract a feature invariant relative to change in a position or a rotation are repeated alternately with each other multiple times. Thus, the feature extraction layer may extract various levels of features from low-level features such as points, lines, and surfaces to complex and meaningful high-level features.

The convolution layer applies a non-linear activation function to a dot product between a filter and a local receptive field for each patch of an input image to obtain the feature map. Compared to other network architectures, a convolutional neural network (CNN) uses a filter having sparse connectivity and shared weights. This connection structure reduces the number of models to be learned, and realizes efficient learning via a backpropagation algorithm, resulting in improved prediction performance.

The pooling layer (or a sub-sampling layer) creates a new feature map by utilizing local information of the feature map obtained from the previous convolution layer. In general, the feature map newly created by the pooling layer is reduced to a smaller size than a size of an original feature map. A typical pooling method includes a max pooling method which selects a maximum value of a corresponding region in the feature map, and an average pooling method which calculates an average of a corresponding region in the feature map. The feature map of the pooling layer is generally less affected by a location of any structure or pattern in the input image than a feature map of the previous layer is. That is, the pooling layer may extract a feature that is more robust to a regional change such as noise or distortion in the input image or the previous feature map. This may play an important role in classification performance. Another role of the pooling layer is to allow a feature of a wider region to be reflected as a layer goes up to a top learning layer in a deep structure. Thus, the features may be created such that as the feature extraction layers are accumulated one on top of another, a lower layer reflects a local feature and a higher layer reflects an abstract feature of an entire image.

In this way, a feature that was finally extracted via repetition of the convolution layer and the pooling layer may be combined with a classification model such as MLP (Multi-Layer Perception) or SVM (Support Vector Machine) in a form of the fully-connected layer and thus may be used for learning and prediction of the classification model.

However, a structure of the DNN according to some embodiments of the present disclosure is not limited thereto. Rather, neural networks of various structures may be employed.

The brain disease prediction method according to some embodiments of the present disclosure as descried above may be implemented as a program or an application to be executed in combination with a computer as hardware, and may be stored in a storage medium included in the brain disease prediction apparatus.

The program may include codes coded in computer languages such as C, C++, JAVA, and machine language that a processor (CPU) of the computer may read through a device interface thereof, in order for the computer to read the program and execute methods implemented using the program. The code may include a functional code related to a function defining functions required to execute the methods, and an execution procedure-related control code necessary for the processor of the computer to execute the functions in a predetermined procedure. Moreover, the code may further include a memory reference-related code indicating a location (address) of an internal memory of the computer or an external memory thereto in which additional information or media necessary for the processor to execute the functions is stored. Moreover, when the processor of the computer needs to communicate with any other remote computer or server to execute the functions, the code may further include a communication-related code indicating how to communicate with any other remote computer or server using a communication module of the computer, and indicating information or media to be transmitted and received during the communication.

The storage medium means a medium that stores data semi-permanently, rather than a medium for storing data for a short moment, such as a register, a cache, or a memory, and that may be readable by a machine. Specifically, examples of the storage medium may include, but may not be limited to, ROM, RAM, CD-ROM, a magnetic tape, a floppy disk, and an optical data storage device. That is, the program may be stored in various recording media on various servers to which the computer may access or on various recording media on the user's computer. Moreover, the medium may be distributed over a networked computer system so that a computer readable code may be stored in a distributed scheme.

The steps of the method or the algorithm described in connection with an embodiment of the inventive concept may be implemented directly in hardware, a software module executed by hardware, or a combination thereof. The software module may reside on Random Access Memory (RAM), Read Only Memory (ROM), Erasable Programmable ROM (EPROM), Electrically Erasable Programmable ROM (EEPROM), Flash Memory, Hard Disk, a removable disk, CD-ROM, or any form of computer readable recording medium well known in the art.

According to the some embodiments of the present disclosure, how the brain disease will develop in the future or how the brain disease will improve when being treated may be predicted based on a size of the brain disease lesion rather than based on each patient.

Moreover, according to some embodiments of the present disclosure, the prediction image to allow predicting the development or improvement of the brain disease based on the voxel-based data-set may be presented. Thus, the user may realistically check the change of the three-dimensional stereoscopic image over time.

Moreover, according to some embodiments of the present disclosure, the probability image may allow the user to intuitively understand a state of a specific new patient. The treatment strategy regarding which treatment is appropriate may be determined based on the image data of the specific new patient.

Moreover, according to some embodiments of the present disclosure, providing a quantitative/real-time probability image may shorten a dosing time of the thrombolytic treatment agent after the cerebral infarction where an initial treatment is important.

Moreover, according to some embodiments of the present disclosure, a large amount of voxel information from data about a small number of patients may be used as the observation. Thus, learning at a big data level may be realized.

The effects of the present disclosure are not limited to the effects mentioned above. Other effects not mentioned will be clearly understood by those skilled in the art from the above description.

While the present disclosure has been described with reference to exemplary embodiments, it will be apparent to those skilled in the art that various changes and modifications may be made without departing from the spirit and scope of the inventive concept. Therefore, it should be understood that the above embodiments are not limiting, but illustrative.

What is claimed is:

1. A method for predicting brain disease state change, being performed by a brain disease prediction apparatus, the method comprising: acquiring, by the brain disease prediction apparatus, a plurality of test images, which comprise images obtained by capturing at least a portion of a human brain at a predetermined time interval; performing, by the brain disease prediction apparatus, a pre-processing procedure of converting the plurality of test images into test voxels configured to be processed for image analysis, wherein a respective test voxel of the test voxels is data composed of three-dimensional voxel units; mapping, by the brain disease prediction apparatus, first and second test voxels selected from the test voxels acquired from a patient, with each other on a three-dimensional voxel unit, wherein the first test voxel is acquired at a first time-point and the second test voxel is acquired at a second time-point, in which a predetermined time has elapsed from the first time-point; generating, by the brain disease prediction apparatus, a voxel-based data-set based on the mapped first and second test voxels; extracting, by the brain disease prediction apparatus, a change in the test voxels by using a deep neural network; and generating, by the brain disease prediction apparatus, a state change probability model based on the change in the test voxels, wherein the generating of the state change probability model further includes: excluding, by the brain disease prediction apparatus, at a predetermined percentage, among measurement values, one or more measurement values having a greater state change rate than a first threshold state change rate, and one or more measurement values having a lower state change rate than a second threshold state change rate.

2. The method of claim 1, wherein the performing of the pre-processing procedure further includes:
correcting, by the brain disease prediction apparatus, an image intensity of each of the plurality of test images using a Gaussian-mixture model (GMM); and
registering, by the brain disease prediction apparatus, the test images having the corrected image intensity based on a standard brain image.

3. The method of claim 1, wherein the test voxels include state information indicating one of a normal state, a cerebral infarction state, and a cerebral hemorrhage state,
wherein the change in the test voxels includes a change from one state of the normal state, the cerebral infarction state, and the cerebral hemorrhage state to another state thereof.

4. The method of claim 1, further comprising:
determining, by the brain disease prediction apparatus, a portion of the test images, to which a stroke is configured to spread; and
performing, by the brain disease prediction apparatus, a labeling operation of an identifiable marker on the determined portion.

5. The method of claim 1, wherein the state change probability model is generated based on at least one of age of the patient, presence or absence of atrial fibrillation of the patient, presence or absence of hypertension of the patient, presence or absence of hyperlipidemia of the patient, drinking experience of the patient, smoking experience of the patient, and presence or absence of diabetes of the patient.

6. The method of claim 1, further comprising:
acquiring, by the brain disease prediction apparatus, a stroke image from the patient;
applying, by the brain disease prediction apparatus, the state change probability model to the stroke image to generate a prediction image visualizing the state change probability model in a three-dimensional manner; and
transmitting, by the brain disease prediction apparatus, the prediction image to a user device.

7. The method of claim 6, further comprising:
deriving, by the brain disease prediction apparatus, a treatment timing based on the prediction image; and
transmitting, by the brain disease prediction apparatus, the derived treatment timing to the user device.

8. The method of claim 6, further comprising:
deriving, by the brain disease prediction apparatus, a treatment strategy based on the prediction image; and
transmitting, by the brain disease prediction apparatus, the derived treatment strategy, to the user device.

9. The method of claim 1, wherein the test images are imaged by a Magnetic resonance imaging (MRI) apparatus.

10. A brain disease prediction apparatus for predicting brain disease state change, the apparatus comprising: a processor; and a memory storing at least one instruction executable by the processor, wherein the at least one instruction is executed by the processor to: acquire a plurality of test images, which comprises images obtained by capturing at least a portion of a human brain at a predetermined time interval; perform a pre-processing procedure of converting the plurality of test images into test voxels configured to be processed for image analysis, wherein a respective test voxel of the test voxels is data composed of three-dimensional voxel units; map first and second test voxels selected from the test voxels acquired from a patient, with each other on a three-dimensional voxel unit, wherein the first test voxel is acquired at a first time-point and a second test voxel is acquired at a second time-point, in which a predetermined time has elapsed from the first time-point; generate a voxel-based data-set based on the mapped first and second test voxels; extract a change in the test voxels using a deep neural network; and generate a state change probability model based on the change in the test voxels, wherein the processor is configured to, in generating the state change probability model, exclude, at a predetermined percentage, among measurement values, one or more measurement values having a greater state change rate than a first threshold state change rate, and one or more measurement values having a lower state change rate than a second threshold state change rate.

11. A non-transitory computer-readable recording medium storing a program for executing the method according to claim 1 in combination with a brain disease prediction apparatus as hardware.

* * * * *